United States Patent
Cho et al.

(10) Patent No.: US 7,329,780 B2
(45) Date of Patent: Feb. 12, 2008

(54) METHOD OF PREPARING OPTICALLY PURE PHENETHYLAMINE DERIVATIVES

(75) Inventors: Seong Hwan Cho, Suwon (KR); Dong Kwon Lim, Yongin (KR); Kwang Hyeg Lee, Seongnam (KR); Yong Sik Youn, Yongin (KR); Choong Sil Park, Icheon (KR)

(73) Assignee: CJ Corporation, Seoul (KR)

( * ) Notice: Subject to any disclaimer, the term of this patent is extended or adjusted under 35 U.S.C. 154(b) by 48 days.

(21) Appl. No.: 10/582,106

(22) PCT Filed: Dec. 9, 2004

(86) PCT No.: PCT/KR2004/003226

§ 371 (c)(1), (2), (4) Date: Jun. 8, 2006

(87) PCT Pub. No.: WO2005/056521

PCT Pub. Date: Jun. 23, 2005

(65) Prior Publication Data

US 2007/0197828 A1    Aug. 23, 2007

(30) Foreign Application Priority Data

Dec. 9, 2003 (KR) .................. 10-2003-0089081

(51) Int. Cl.
*C07C 303/40* (2006.01)
*C07C 311/37* (2006.01)

(52) U.S. Cl. ............. 564/86; 564/138; 564/139; 564/143; 564/144; 564/414

(58) Field of Classification Search .............. None
See application file for complete search history.

(56) References Cited

U.S. PATENT DOCUMENTS

| 4,217,305 A | 8/1980 | Imai et al. |
| 4,373,106 A | 2/1983 | Imai et al. |
| 4,880,841 A | 11/1989 | Imai et al. |

FOREIGN PATENT DOCUMENTS

| CA | 1282077 | 3/1991 |
| EP | 0257787 A1 | 3/1988 |
| JP | 02-295967 A | 12/1990 |
| JP | 02-306958 A | 12/1990 |
| JP | 2000-229901 A | 8/2000 |
| KR | 1994-0007746 B1 | 8/1994 |

*Primary Examiner*—Brian Davis
(74) *Attorney, Agent, or Firm*—Rothwell, Figg, Ernst & Manbeck P.C.

(57) ABSTRACT

Provided is a method of preparing an optically pure compound having formula 1 or its salts. The method includes: reacting (R)-2-(4-methoxy-3-aminosulfonyl-phenyl)-1-methylethylamine or its salts with a compound selected from the group consisting of chloroacetic acid, bromoacetic acid, fluoroacetic acid, iodoacetic acid, α-halogenoacetic acid anhydride, and α-halogenoacetyl halide in the presence of a base or an acylating agent.

6 Claims, No Drawings

METHOD OF PREPARING OPTICALLY PURE PHENETHYLAMINE DERIVATIVES

CROSS REFERENCE TO RELATED APPLICATION

This application is a 35 U.S.C. § 371 National Phase Entry Application from PCT/KR2004/003226, filed Dec. 9, 2004, and designating the United States.

BACKGROUND OF THE INVENTION

1. Field of the Invention

The present invention relates to a method of preparing an optically pure phenethylamine derivative which is an intermediate useful for preparing tamsulosin or its salts and a method of preparing tamsulosin or its salts using the optically pure phenethylamine derivative.

2. Description of the Related Art

Tamsulosin or its salts (for example, hydrochloride) exhibit an action of blocking α-adrenaline and are known as therapeutic agents for benign prostatic hypertrophy, hypertension, and congestive heart failure. The chemical name of tamsulosin is (R)-5-{2-[2-(2-ethoxyphenoxy)ethylamino]-propyl}-2-methoxybenzenesulfonamide and has an asymmetric carbon as seen from the following chemical structure. Thus, there is a need to obtain said compound in an optically pure form, i.e., (R)-form.

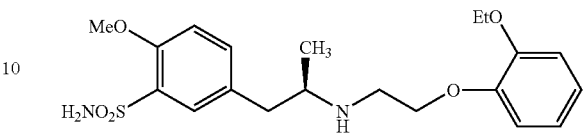

U.S. Pat. Nos. 4,217,305 and 4,373,106 describe methods of preparing tamsulosin or its salts using racemic compounds, as shown in scheme 1. However, in these methods, the compounds in racemic forms are obtained by using achiral compounds as the starting materials, and thus, a single isomeric compound cannot be easily isolated from the obtained compounds. Especially, the single isomeric compound cannot be obtained in about 50% or more, thereby resulting low yield.

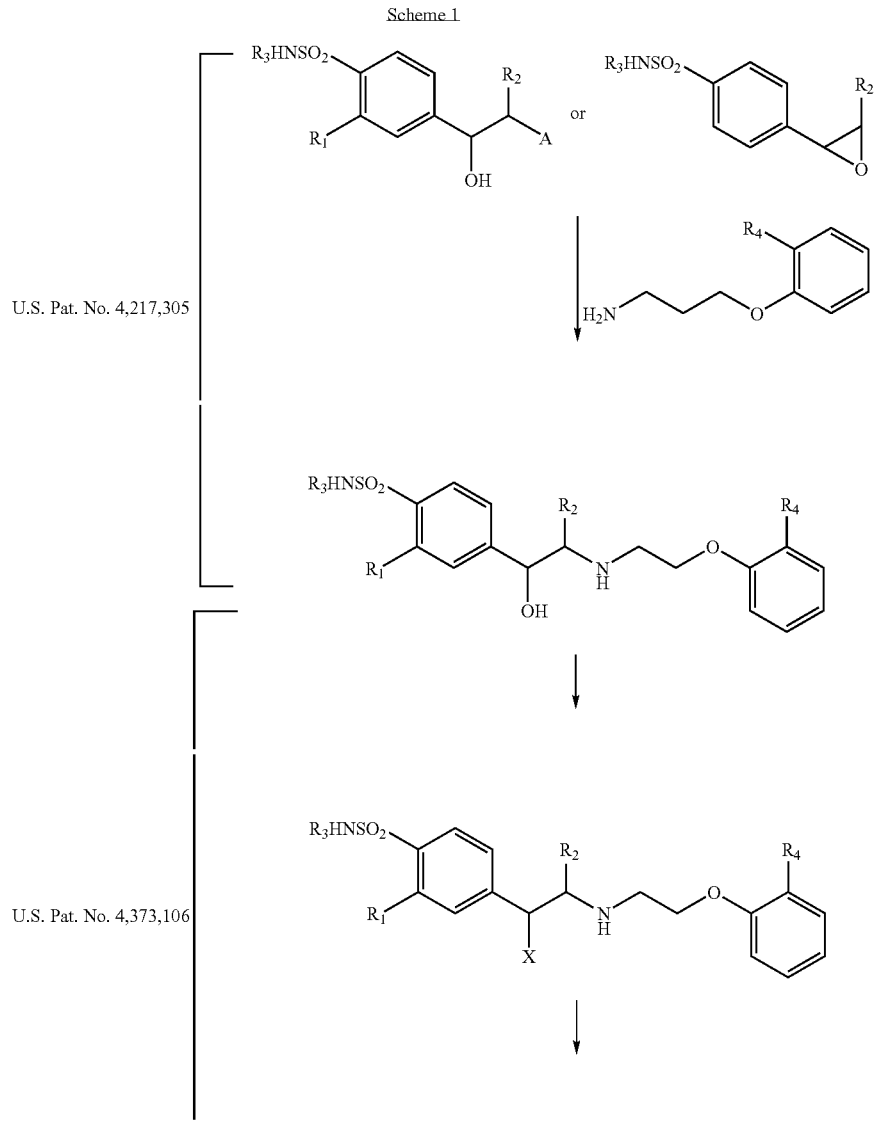

Scheme 1

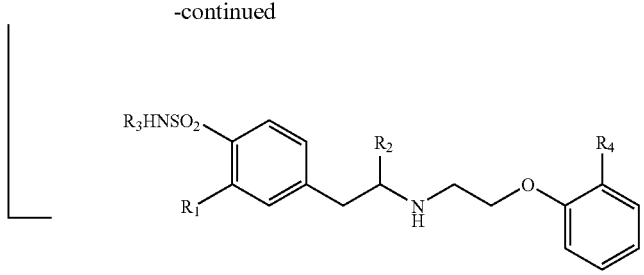

Korean Laid-Open Patent Publication No. 1994-7746 describes a method of preparing tamsulosin or its hydrochloride using a chiral amine, as shown in scheme 2. However, in the N-akylating reaction, which is a main reaction of the method, reactants are primary amines, and thus, a side reaction, such as alkylation, of the reactants, can occur. A sulfonamide group can also be subjected to alkylation, and thus, a side reaction can occur. Accordingly, the reaction yield is low and products of the side reactions should be separately removed.

Scheme 2

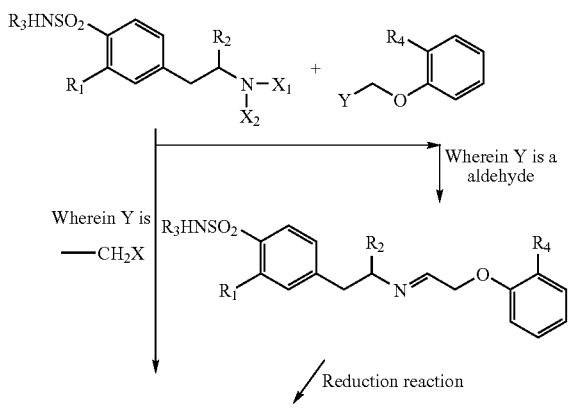

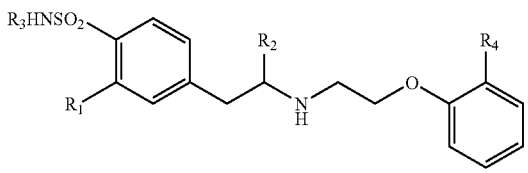

Japanese Laid-Open Patent Publication Nos. Hei 2-295967 and 2-306958 describe methods of preparing tamsulosin and its hydrochloride. In the methods, 2-(4-methoxyphenyl)-1-methylethylamine, which does not have an aminosulfonyl group, as a starting material was reacted with bromoacetyl chloride, etc. in an N-alkylation reaction and an aminosulfonyl group was introduced into the resultant product to obtain an intermediate. Then, the intermediate was reacted with ethoxy phenol and reduced.

Scheme 3

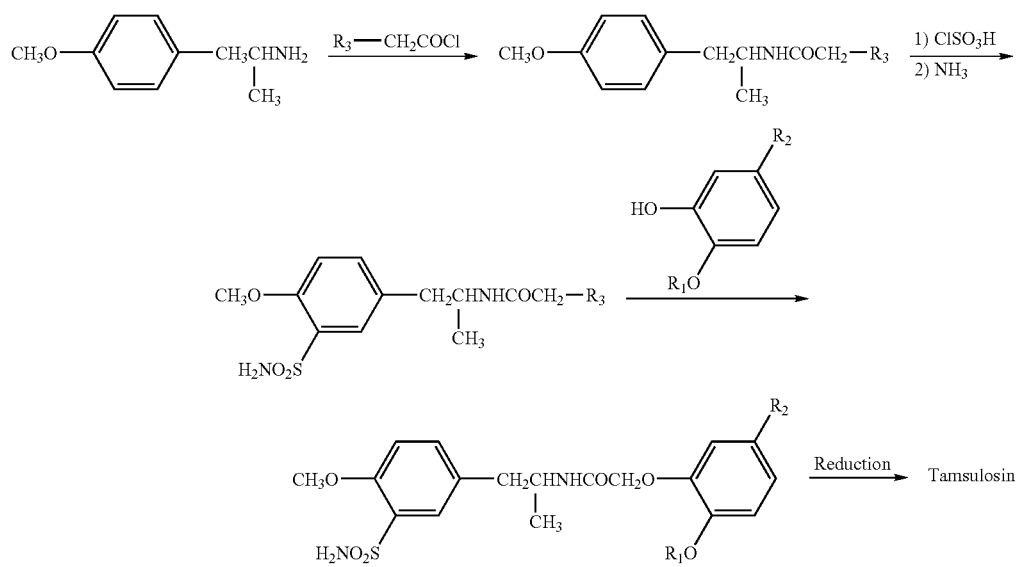

However, in this method, the compound which does not have an aminosulfonyl group should be used to prevent a side reaction occurring due to the use of highly reactive reactants, such as acid chloride, etc. Further, a further reaction process should be performed, i.e., the introduction of an aminosulfonyl group into the resultant product.

Thus, a method of preparing tamsulosin or its salts which can prevent a side reaction and formation of racemic compounds and increase an yield of production is required.

SUMMARY OF THE INVENTION

The present inventors conducted research to develop an improved method of preparing tamsulosin or its hydrochloride and discovered that when halogenoacetic acid, α-halogenoacetic acid anhydride, or α-halogenoacetyl halide are reacted with an optically pure compound having both an aminosulfonyl group and a methoxy group, a separate process of introduction of the aminosulfonyl group into a product is not required and a highly optically pure intermediate compound useful for preparing tamsulosin or its salts can be obtained with high efficiency.

The present invention provides a method of preparing an optically pure phenethylamine derivative which is an intermediate useful for preparing tamsulosin or its salts.

The present invention also provides a method of preparing tamsulosin or its salts using an optically pure phenethylamine derivative prepared using the above method.

DETAILED DESCRIPTION OF THE INVENTION

According to an embodiment of the present invention, there is provided a method of preparing an optically pure compound having formula 1 or its salts, comprising:

reacting (R)-2-(4-methoxy-3-aminosulfonyl-phenyl)-1-methylethylamine or its salts with a compound selected from the group consisting of chloroacetic acid, bromoacetic acid, fluoroacetic acid, iodoacetic acid, αhalogenoacetic acid anhydride, and α-halogenoacetyl halide in the presence of a base or an acylating agent:

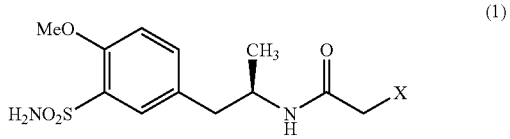

(1)

wherein

X is halogen.

(R)-2-(4-methoxy-3-aminosulfonyl-phenyl)-1-methylethylamine or its salts are commercially available. Chloroacetic acid, bromoacetic acid, fluoroacetic acid, iodoacetic acid, etc. are also commercially available. α-halogenoacetic acid anhydride may be obtained by reacting α-halogenoacetic acid with carboxylic acid. For example, α-halogenoacetic acid anhydride may be obtained by reacting fluoroacetic acid, chloroacetic acid, bromoacetic acid, or iodoacetic acid with carboxylic acid. α-halogenoacetic acid anhydride used in an embodiment of the present invention may be added to the reaction or produced in-situ during the reaction. For example, α-halogenoacetic acid anhydride may be obtained by α-halogenoacetic acid with a carboxylic acid selected from the group consisting of methyl chloroformate, ethyl chloroformate, butyl chloroformate, benzyl chloroformate, and pivaloyl chloride in the presence of an inert solvent and a base catalyst. In an embodiment of the present invention, examples of α-halogenoacetyl halide include, but are not limited to, fluoroacetyl fluoride, chloroacetyl chloride, bromoacetyl bromide, and iodoacetyl iodide. α-halogenoacetyl halide is commercially available or may be obtained using a conventional method by halogenating carboxylic acid of α-halogenoacetic acid. For example, α-halogenoacetyl chloride may be obtained by reacting α-halogenoacetic acid with $SOCl_2$, $PCl_3$, or $PCl_5$.

The compound selected from the group consisting of chloroacetic acid, bromoacetic acid, fluoroacetic acid, iodoacetic acid, α-halogenoacetic acid anhydride, and α-halogenoacetyl halide may be used in a slight excess amount, based on an amount of (R)-2-bromo-N-[2-(4-methoxy-3-aminosulfonyl-phenyl)-1-methylethyl]acetamide or its salts, which is expensive. For example, the compound may be used in an amount of about 1 to 4 equivalents per equivalent of (R)-2-(4-methoxy-3-aminosulfonyl-phenyl)-1-methylethylamine or its salts.

Examples of the base used in the method according to an embodiment of the present invention incude trialkylamine or an inorganic base. Examples of the trialkylamine include trimethylamine, triethylamine, or diisopropylethylamine. Preferably, triethylamine is used. Examples of the inorganic base include a conventional inorganic base, such as $K_2CO_3$, $Na_2CO_3$, $KHCO_3$, or $NaHCO_3$. The inorganic base may be used in an amount of about 1 to 4 equivalents per equivalent of (R)-2-(4-methoxy-3-aminosulfonyl-phenyl)-1-methylethylamine or its salts.

Examples of the acylating agent used in the method according to an embodiment of the present invention include N,N'-dicyclohexylcarbodiimide, N,N'-diisopropylcarbodiimide, N-[3-(dimethylaminopropyl)-N'-ethylcarbodiimide, bis(2-oxo-3-oxazolidinyl)phosphinic chloride, (benzotriazole-1-yloxy)tris(dimethylamino)phosphonium hexafluorophosphate, O-benzotriazole-1-yl-N,N,N',N'-bis(tetramethyl) uronium hexafluorophosphate, O-(7-azabenzotriazole-1-yl)-N,N,N',N'-tetramethyluronium hexafluorophosphate, ethyl chloroformate, methyl chloroformate, butyl chloroformate, or benzyl chloroformate. Preferably, ethyl chloroformate is used. The acylating agent may be used in an amount of about 1 to 4 equivalents per equivalent of (R)-2-(4-methoxy-3-aminosulfonyl-phenyl)-1-methylethylamine or its salts.

In the method according to an embodiment of the present invention, a conventional polar or non-polar organic solvent, for example, dimethylsulfoxide, dimethyl formamide, dimethyl acetamide, tetrahydrofuran, methylene chloride, etc. may be used. Preferably, tetrahydrofuran or methylene chloride is used. The reaction temperature may be about −50 to 50° C., preferably about 0 to 5° C.

According to another embodiment of the present invention, there is provided a method of preparing (R)-5-{2-[2-(2-ethoxyphenoxy)ethylamino]-propyl}-2-methoxy-benzenesulfonamide or its salts, comprising:

reacting an optically pure compound having formula 1 or its salts prepared using the above method with (i) 2-ethoxyphenol in the presence of a base or (ii) sodium 2-ethoxyphenoxide or potassium 2-ethoxyphenoxide to prepare (R)-2-(2-ethoxyphenoxy)-N-[2-(4-methoxy-3-aminosulfonyl-phenyl)-1-methyl-ethyl]acetamide; and reducing the obtained (R)-2-(2-ethoxyphenoxy)-N-[2-(4-methoxy-3-aminosulfonyl-phenyl)-1-methylethyl]acetamide.

The method according to the present embodiment may be performed as described in Japanese Laid-Open Patent Publication Nos. Hei 2-295967 and 2-306958.

The preparation of (R)-2-(2-ethoxyphenoxy)-N-[2-(4-methoxy-3-aminosulfonyl-phenyl)-1-methylethyl]acetamide may be performed in an organic solvent, such as dimethyl formamide, dimethylsulfoxide, dimethyl acetamide, tetrahydrofuran, acetone, or methylene chloride, preferably dimethyl formamide, tetrahydrofuran, or acetone and at a temperature of −20 to 100° C., preferably about 25 to 60° C. Examples of the base include $K_2CO_3$, potassium tert-butoxide, NaOH, NaH, KOH, KH, LiOH, or LiH. Preferably, $K_2CO_3$ or potassium tert-butoxide, etc. is used.

The reduction of (R)-2-(2-ethoxyphenoxy)-N-[2-(4-methoxy-3-aminosulfonyl
-phenyl)-1-methylethyl]acetamide may be performed using about 2 to 6 equivalents of sodium borohydride-boron trifluoride (NaBH4-BF3 etherate) or lithium aluminum hydride, etc. in an organic solvent, such as dimethyl formamide, dimethylsulfoxide, dimethyl acetamide, tetrahydrofuran, ethanol, methanol, acetone, or methylene chloride, preferably tetrahydrofuran. The reduction temperature may be about 0 to 80° C.

The resultant compound, (R)-5-{2-[2-(2-ethoxyphenoxy)ethylamino]-propyl}-2-methoxybenzenesulfonamide (i.e., tamsulosin) can be obtained in a form of an inorganic acid salt by adding a conventional inorganic acid, such as anhydrous hydrochloric acid.

The intermediate of formula 1 and tamsulosin and their salts prepared using the methods according to embodiments of the present invention can be isolated and purified using conventional methods, such as chromatography or recrystallization, etc. Preferably, recrystallization is used, since economical industrial mass-production can be facilitated.

Both the method of preparing the intermediate of formula 1 or its salts and the method of preparing tamsulosin or its salts according to embodiments of the present invention are represented by scheme 4:

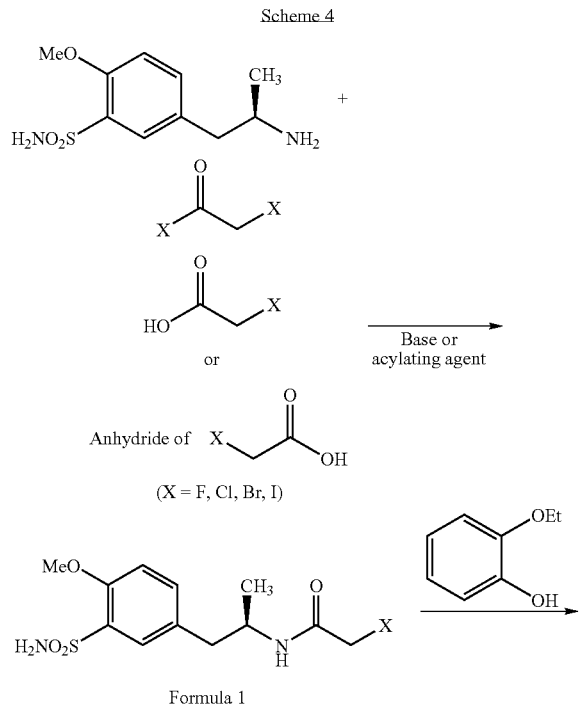

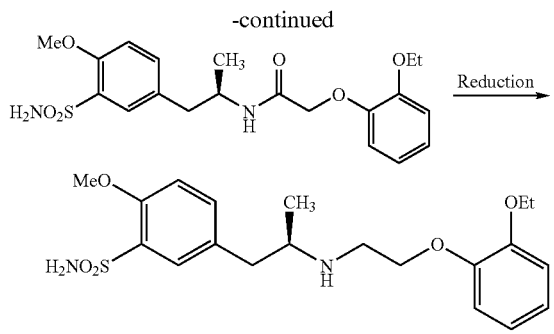

Hereinafter, the present invention will be described in more detail with reference to the following examples. However, these examples are given for the purpose of illustration and are not intended to limit the scope of the invention.

EXAMPLES

Example 1

Preparation of (R)-2-bromo-N-[2-(4-methoxy-3-aminosulfonyl-phenyl)-1-methyl-ethyl]-acetamide)

1.0 g of (R)-2-(4-methoxyphenyl-3-aminosulfonyl-phenyl)-1-methylethylamine was dissolved in 50 ml of methylene chloride. 0.72 g (2.0 eq) of triethyamine was added to the resultant solution and cooled to 0 to 5° C. Then, 1.44 g (2.0 eq) of bromoacetyl bromide was added dropwise to the resultant solution and stirred at 0 to 5° C. After it was confirmed by HPLC that the starting materials were completely consumed, 100 ml of ethyl acetate and then 50 ml of 10% HCl were added to the resultant solution and stirred. The ethyl acetate layer was separated and washed with 50 ml of a 10% $K_2CO_3$ solution and dried over $MgSO_4$, and then, filtered and concentrated. The obtained concentrate was dissolved in ethyl acetate and recrystallized with hexane to obtain the title compound (1.2 g).

Yield: 80.0% NMR(DMSO-$d_6$):1.15(3H, d), 2.6~2.8(2H, m), 3.8(2H, s), 3.90(4H, s), 7.0(2H, s), 7.1(1H, d),7.4(1H, d), 7.6(1H, d), 8.21(2H, d). $[\alpha]^{24}D$=+5.0 (C=1, MeOH)

Example 2

Preparation of (R)-2-bromo-N-[2-(4-methoxy-3-aminosulfonyl-phenyl)-1-methyl-ethyl]-acetamide)

Bromoacetic acid (3.4 g) was dissolved in 50 ml of methylene chloride. 2.3 g of triethyamine was added to the resultant solution and cooled to −40 to −45° C. Then, 2.66 g of ethyl chloroformate was added dropwise to the resultant solution and stirred at −40 to −45° C. for 4 hours. 3.0 g of (R)-2-(4-methoxyphenyl-3-aminosulfonyl-phenyl)-1-methylethylamine was added to the resultant product and stirred at −40 to −45° C. for 1.5 hours. Then, 50 ml of 10% HCl were added to the resultant solution and stirred. The organic layer was separated and washed with 50 ml of 10% $K_2CO_3$ solution and dried over $MgSO_4$, and then, filtered and concentrated. The obtained concentrate was dissolved in methanol and recrystallized with hexane to obtain the title compound as a white solid (4.0 g).

Yield: 89.2% NMR: as described in Example 1 $[\alpha]^{24}D$=+5.0 (C=1, MeOH)

Example 3

Preparation of (R)-2-chloro-N-[2-(4-methoxy-3-aminosulfonyl-phenyl)-1-methyl-ethyl]-acetamide)

The title compound (1.2 g) was prepared in the same manner as in Example 1, except that 1.05 g (2.0 eq) of chloroacetyl chloride was used instead of bromoacetyl bromide.

Yield: 92.3% NMR(DMSO-d6): 1.15(3H, d), 2.6~2.8(2H, m), 3.8(2H, s), 3.90(4H, s), 7.0(2H, s), 7.1(1H, d),7.4(1H, d), 7.6(1H, d), 8.21(2H, d) $[\alpha]^{24}D=-2.0$ (C=1, MeOH)

Example 4

Preparation of (R)-2-(2-ethoxyphenoxy)-N-[2-(4-methoxy-3-aminosulfonyl-phenyl)-1-methyl-ethyl]-acetamide 1.0 g of (R)-2-bromo-N-[2-(4-methoxy-3-aminosulfonyl-phenyl)-1-methyl-ethyl]-acetamide prepared in Example 2 was added to a stirring solution of 1.25 g of potassium t-butoxide and 1.5 g of 2-ethoxy phenol in 10 ml of tetrahydrofuran and stirred at 25° C. for 1 hour. After the reaction was completed, 50 ml of a 10% hydrochloric acid solution and then, 50 ml of ethyl acetate was added to the resultant solution and then, extracted. Next, the organic layer was separated and concentrated. 10 ml of methanol was added to the obtained concentrated residue and stirred for 12 hours. Then, the resultant product was filtered and dried to obtain the title compound as a white solid (0.9 g).

Yield: 77.8% NMR(DMSO-$d_6$): 1.15(3H, d), 1.25(3H, t), 2.8(1H, m), 3.6(2H, s) 3.90(3H, s 4.05(2H, q), 6.9~7.1(4H, m), 7.0(2H, s), 7.1(1H, d),7.4(1H, d), 7.6(1[$\alpha$]$^{24}$D=−38.2 (C=1.0, CH$_3$CN)

Example 5

Preparation of (R)-5-{2-[2-(2-ethoxyphenoxy)ethylamino]-propyl}-2-methoxy-benzenesulfonamide)

5.39 g of sodium borohydride was dissolved in 200 ml of tetrahydrofuran and 23.4 ml of boron trifluoride was added to the resultant solution at room temperature and stirred for 15 minutes. 27.0 g of (R)-2-(2-ethoxyphenoxy)-N-[2-(4-methoxy-3-aminosulfonyl-phenyl)-1-methyl-ethyl]acetamide was added in aliquots to the resultant solution, refluxed for 15 minutes, and cooled. 70 ml of a 10% aqueous solution of hydrochloric acid was added to the cooled mixture and again refluxed for 30 minutes. The resultant solution was made alkali by adding a 10% K$_2$CO$_3$ solution and evaporated to remove tetrahydrofuran. An aqueous layer was extracted with ethyl acetate and dried and concentrated to obtain white crystals (33.5 g). The obtained crystals were dissolved in ethanol and a concentrated aqueous solution of hydrochloric acid was added to the resultant solution to obtain white crystals. The obtained white crystals were filtered to obtain a product (25 g) which was recrystallized with a mixture of ethanol-water (4:1). Thus, the title compound was obtained in a form of hydrochloride as white pure crystals.

Yield: 92.5% NMR(DMSO-$d_6$): 1.15(3H, d), 1.25(3H, t), 2.65~3.25(2H, dd), 3.40~3.55(3H, m), 3.90(3H, s), 4.05(2H, q), 4.25(2H, t), 6.9(2H, s), 6.9~7.7(7H, Bz), 9.2(2H, s) M.P : 226~229° C. [$\alpha$]$^{24}$D=−4.1(C=0.35, methanol)

According to the present invention, a highly optically pure intermediate compound of formula 1, which is useful for preparing tamsulosin, or its salts can be prepared with high efficiency without causing side reactions and without a separate process of introduction of an aminosulfonyl group. Further, according to the present invention, tamsulosin or its hydrochloride can be prepared with high efficiency and high optical purity using the above intermediate compound.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of preparing an optically pure compound having formula 1 or its salts, comprising:
    reacting (R)-2-(4-methoxy-3-aminosulfonyl-phenyl)-1-methylethylamine or its salts with a compound selected from the group consisting of chloroacetic acid, bromoacetic acid, fluoroacetic acid, iodoacetic acid, α-halogenoacetic acid anhydride, and α-halogenoacetyl halide in the presence of a base or an acylating agent:

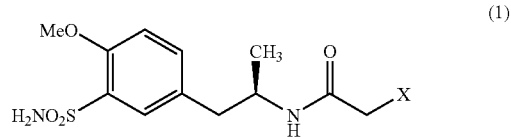

(1)

wherein
    X is halogen.

2. The method of claim 1, wherein the base is trialkylamine or an inorganic base.

3. The method of claim 1, wherein the acylating agent is N,N'-dicyclohexylcarbodiimide, N,N'-diisopropylcarbodiimide, N-[3-(dimethylaminopropyl)-N'-ethylcarbodiimide, bis(2-oxo-3-oxazolidinyl)phosphinic chloride, (benzotriazole-1-yloxy)tris(dimethylamino)phosphonium hexafluorophosphate, O-benzotriazole-1-yl-N,N,N',N'-bis(tetramethyl)uronium hexafluorophosphate, or O-(7-azabenzotriazole-1-yl)-N,N,N',N'-tetramethyluronium hexafluorophosphate.

4. The method of claim 1, wherein a-halogenoacetic acid anhydride is obtained in situ during the reaction by reacting α-halogenoacetic acid with at least one compound selected from the group consisting of methyl chloroformate, ethyl chloroformate, butyl chloroformate, benzyl chloroformate, and pivaloyl chloride.

5. The method of claim 1, wherein α-halogenoacetyl halide is selected from the group consisting of bromoacetyl bromide, bromoacetyl chloride, chloroacetyl chloride, and chloroacetyl bromide.

6. A method of preparing (R)-5-{2-[2-(2-ethoxyphenoxy) ethylamino]-propyl}-2-methoxybenzenesulfonamide or its salts, comprising:
    reacting an optically pure compound having formula 1 or its salts prepared using the method of claim 1 with (i) 2-ethoxyphenol in the presence of a base or (ii) sodium 2-ethoxyphenoxide or potassium 2-ethoxyphenoxide to prepare (R)-2-(2-ethoxyphenoxy)-N-[2-(4-methoxy-3-aminosulfonyl-phenyl)-1-methyl-ethyl]acetamide; and
    reducing the obtained (R)-2-(2-ethoxyphenoxy)-N-[2-(4-methoxy-3-aminosulfonyl-phenyl)-1-methylethyllacetamide.

* * * * *